(12) United States Patent
Motouri et al.

(10) Patent No.: US 8,647,619 B2
(45) Date of Patent: Feb. 11, 2014

(54) OSTEOGENESIS PROMOTER

(75) Inventors: Mutsumi Motouri, Tokorozawa (JP); Hiroaki Matsuyama, Kawagoe (JP); Yoshikazu Morita, Kawagoe (JP); Atsushi Serizawa, Kawagoe (JP); Hiroshi Kawakami, Kawagoe (JP)

(73) Assignee: Megmilk Snow Brand Co., Ltd., Sapporo (JP)

( * ) Notice: Subject to any disclaimer, the term of this patent is extended or adjusted under 35 U.S.C. 154(b) by 745 days.

(21) Appl. No.: 12/573,413

(22) Filed: Oct. 5, 2009

(65) Prior Publication Data

US 2010/0209412 A1 Aug. 19, 2010

Related U.S. Application Data

(63) Continuation-in-part of application No. 10/566,711, filed as application No. PCT/JP2004/011689 on Aug. 13, 2004, now abandoned.

(30) Foreign Application Priority Data

Aug. 15, 2003 (JP) ................................ 2003-293829

(51) Int. Cl.
  *A61K 38/43* (2006.01)
(52) U.S. Cl.
  USPC ........................................................ 424/94.1

(58) Field of Classification Search
  None
  See application file for complete search history.

(56) References Cited

U.S. PATENT DOCUMENTS

| 4,726,948 A | 2/1988 | Prieels et al. |
| 5,932,259 A | 8/1999 | Kato et al. |

FOREIGN PATENT DOCUMENTS

| JP | 61-083131 | 4/1986 |
| JP | 2-048534 | 2/1990 |
| JP | 5-124980 | 5/1993 |
| JP | 8-151331 | 6/1996 |
| JP | 8-165249 | 6/1996 |
| JP | 2002-544212 | 12/2002 |

OTHER PUBLICATIONS

Japanese Patent Office issued a Japanese Office Action dated Oct. 27, 2009, Application No. 2003-293829.

*Primary Examiner* — Debbie K Ware
(74) *Attorney, Agent, or Firm* — Young & Thompson

(57) ABSTRACT

It is intended to provide an osteogenesis promoter capable of promoting osteogenesis by promoting the differentiation of osteoblasts, and foods, drinks, drugs or feeds for promoting osteogenesis. Namely, an osteogenesis promoter capable of promoting osteogenesis by promoting the differentiation of osteoblasts which comprises, as the active ingredient, lactoperoxidase and/or a digestion product obtained by digesting lactoperoxidase with a protease such as trypsin; and foods, drinks, drugs or feeds for promoting osteogenesis containing lactoperoxidase and/or its digestion product.

4 Claims, 1 Drawing Sheet

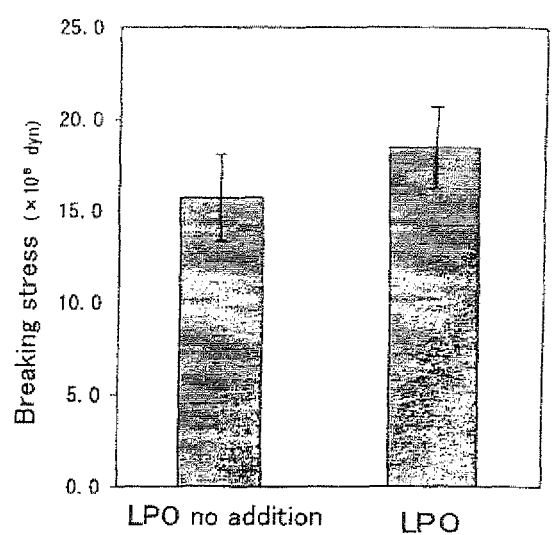

OSTEOGENESIS PROMOTER

This application is a continuation-in-part application of application Ser. No. 10/566,711 filed Mar. 15, 2006, now abandoned, which is a National phase of PCT/JP2004/011689 filed Aug, 13, 2004, which claims priority of application Ser. No. 2003-293829 filed Aug. 15, 2003. The entire contents of each of the above-identified applications are hereby incorporated by reference.

TECHNICAL FIELD

The present invention relates to an osteogenesis promoter which includes lactoperoxidase and/or a digestion product thereof as an effective component. Moreover, the invention relates to foods, drinks, drugs, or feeds for promoting osteogenesis which contains lactoperoxidase and/or a digestion product thereof.

BACKGROUND ART

In recent years, various bone diseases such as osteoporosis, bone fractures, and lumbago have increased along with the progressive increase in the elderly population. In a bone tissue, osteogenesis and bone resorption constantly occur. In a young person, a balance between osteogenesis and bone resorption is kept, but the balance is disrupted to bone resorption owing to various causes with aging (uncoupling). Continuance of this state for a long period of time makes the bone tissue fragile, resulting in occurrence of various bone diseases such as osteoporosis, bone fractures, and lumbago. It is considered that prevention of the uncoupling enables prevention of various bone diseases such as osteoporosis, bone fractures, and lumbago.

Conventionally, to prevent the uncoupling and to prevent or treat various bone diseases such as osteoporosis, bone fractures, and lumbago, the following methods have been performed: (1) calcium supplementation by diet, (2) light exercise, (3) insolation, (4) medication, and the like. For calcium supplementation by diet, there are used calcium salts such as calcium carbonate and calcium phosphate and natural calcium agents such as eggshell and fish bone powder. However, they are not completely suitable materials for oral ingestion. For light exercise, it is said that jogging or walking is good. However, a person whose body has weakened tends to think very troublesome to perform even light exercise, and a bed-ridden elderly is scarcely able to exercise. Insolation is said to be good in the light of supplementation of activated vitamin D3. However, even if only insolation is performed, only insufficient effects are obtained. For administration of a drug, there are used 1-α-hydroxyvitamin D3, a calcitonin preparation, and the like, which are known to be effective for treating osteoporosis. However, those substances are drugs themselves and cannot be used as food materials.

On the other hand, the inventors of the present invention have searched for an osteogenesis promoting factor and a bone resorption inhibiting factor in milk to obtain substances that have an osteogenesis promoting effect and a bone resorption inhibiting effect and can be used as food materials. In the process, the inventors of the present invention have found out that lactoperoxidase promotes osteoblast differentiation to have an osteogenesis promoting effect. The osteoblast is a cell playing a major role in osteogenesis, which is present on the surface of a bone tissue and secretes bone matrix proteins. Crystals of calcium phosphate are deposited on the bone matrix proteins to form hard bone tissues.

On the other hand, an osteoclast is a cell that is generated from a hematopoietic stem cell, which is present on the surface of a spongy bone and dissolves the bone. It is considered that an osteoclast dissolves a bone matrix (bone resorption), and then an osteoblast synthesizes a bone matrix, resulting in occurrence of bone formation, growth (modeling), or metabolism (remodeling). The invention of the present application has been found out that lactoperoxidase promotes differentiation of an osteoblast that plays a major role of osteogenesis in the bone metabolism to have an osteogenesis promoting effect and to have a bone strengthening effect.

Lactoperoxidase is present in milk in large amounts and is a glycoprotein that contains heme iron and has a molecular weight of about 80,000. The lactoperoxidase content in bovine milk is higher than that in human milk. The content in human milk is 0.01 mg/100 ml or less, while the content in bovine milk is about 3 mg/100 ml. A function of lactoperoxidase includes oxidation of various substances in the presence of hydrogen peroxide. That is, hypothiocyanate ($OSCN^-$) generated in the case of oxidation of thiocyanate ($SCN^-$) by lactoperoxidase inhibits proliferation of a certain kind of microorganism. $SCN^-$ is a metabolite in a living body and is generally present in milk, so that proliferation of a microorganism producing hydrogen peroxide is inhibited by lactoperoxidase in milk. As described above, lactoperoxidase is considered to act as one of antibacterial effects of milk, which is also referred to as a lactoperoxidase system. With regard to use of lactoperoxidase, there are known a technique to maintain an appropriate sourness of a product during the best-before period by blending lactoperoxidase in fermented milk to suppress excessive increase in the sourness during circulation and preservation of the product (see, for example, Patent Document 1), an aging preventing agent (see, for example, Patent Document 2), a low cariogenic nutritive agent (see, for example, Patent Document 3), an agent for treatment of animal dermatosis (see, for example, Patent Document 4), and the like. However, the fact that lactoperoxidase has an osteoblast differentiation promoting effect has not been clarified yet, and therefore lactoperoxidase is not used for bone strengthening.

For a bone strengthening effect of milk, the inventors of the present invention have found out that basic proteins, which are present in minute amounts in milk, have an osteoblast proliferation promoting effect, a bone strengthening effect, and a bone resorption inhibiting of effect, and they have applied for a patent (see, for example, Patent Document 5). However, it is not known that lactoperoxidase contained in the basic proteins has an osteogenesis promoting effect.

Patent Document 1: WO 92/13064
Patent Document 2: JP 05-124980 A
Patent Document 3: JP 09-107917 A
Patent Document 4: JP 07-233086 A
Patent Document 5: JP 08-151331 A

DISCLOSURE OF THE INVENTION

Problems to be Solved by the Invention

In the course of search for a substance having an osteoblast proliferation promoting effect, a bone strengthening effect, and a bone resorption preventing effect, the inventors of the present invention have found out that lactoperoxidase promotes osteoblast differentiation to have an osteogenesis promoting effect and a bone strengthening effect. Also, they have found out that a digestion product of lactoperoxidase promotes osteoblast differentiation to have the same effects, thereby completing the present invention.

Accordingly, an object of the present invention is to provide a novel osteogenesis promoter which includes lactoperoxidase and/or a digestion product thereof as an effective component. Moreover, an object of the present invention is to provide foods, drinks, drugs, or feeds each of which are imparted with an osteogenesis promoting effect by blending with lactoperoxidase and/or a digestion product thereof.

Considering the nature of the disease of osteoporosis, an object of the present invention is to provide an osteogenesis promoter and foods, drinks, drugs, or feeds for promoting osteogenesis, which can be directly and orally ingested over a longtime in daily meals without any problems in preference, exert an osteogenesis promoting effect on bones directly, and therefore is expected as efficacious in preventing or ameliorating/treating osteoporosis.

Means for Solving the Problems

Lactoperoxidase is prepared from mammal's milk. Examples of its source include milk of a bovine, buffalo, human, swine, sheep, goat, horse, or the like. Lactoperoxidase is a known substance and can be produced by a known method: for example, a milk material such as skim milk or whey is brought into contact with a cation-exchange resin to adsorb basic proteins thereon, and the proteins were eluted at a salt concentration of 0.1 to 1.0 M, followed by desalting and concentration by means of a reverse osmosis (RO) membrane, electrodialysis (ED), etc, and drying if necessary. Meanwhile, a method of purifying lactoperoxidase using a sulfonated carrier (JP 03-109400 A) can be advantageously used for industry. Meanwhile, in the present invention, there may also be used lactoperoxidase produced by a genetic engineering technique, for example, a recombinant LPO described in WO 91-06639 or the like. Note that lactoperoxidase is marketed as a product and is sold by Sigma, Sederma, etc.

Methods for increasing the purity of lactoperoxidase include cation exchange resin, affinity chromatography, hydroxyapatite chromatography, etc.

The digestion product of lactoperoxidase is a peptide mixture obtained by digesting the above-described lactoperoxidase with a protease such as trypsin, pancreatin, chymotrypsin, pepsin, papain, kallikrein, cathepsin, thermolysin, or V8 protease, and lactoperoxidase is preferably digested so as to have a molecular weight of 10,000 or less.

Effect of the Invention

An osteogenesis promoter which includes lactoperoxidase and/or a digestion product thereof as an effective component, and foods, drinks, drugs, feeds for promoting osteogenesis which contain lactoperoxidase and/or a digestion product thereof of the present invention promote osteoblast differentiation to promote an osteogenesis effect, so that they have a bone strengthening effect and are useful for preventing or ameliorating various bone diseases such as osteoporosis, or the like. In addition, an osteogenesis promoter and foods or drinks for promoting osteogenesis of the present invention have advantages that they are formed from materials that are easily available, they always have consistent qualities, they can be produced inexpensively without requiring complex processes, and they can be prepared in large amounts.

BRIEF DESCRIPTION OF THE DRAWING

FIG. 1 shows comparison of the rupture stress of the femora of osteoporosis rats in the case of administration of lactoperoxidase obtained in Example 1 of the present invention to the rats with that of controls (no lactoperoxidase added).

BEST MODE FOR CARRYING OUT THE INVENTION

When an osteogenesis promoter of the present invention is administered, lactoperoxidase and/or a digestion product thereof can be used without modification. However, if necessary, they can be used after being diluted with lactose, starch, or the like to produce powders, granules, tablets, or capsules or after being formulated into drinks or the like in accordance with a conventional method. Moreover, osteogenesis can be promoted by blending lactoperoxidase and/or a digestion product thereof in foods or drinks such as milk, milk beverage, coffee drinks, juices, jellies, biscuits, breads, noodles, and sausages to promote osteoblast differentiation. Furthermore, concomitant use of an absorbable calcium preparation containing calcium chloride, calcium carbonate, calcium lactate, eggshell, milk-derived calcium, or the like may further enhance the osteogenesis promoting effect. Meanwhile, osteogenesis of a livestock, fowl, or the like can be promoted by blending those effective components in feeds.

To obtain the osteogenesis promoting effect, an adult desirably orally ingests as an effective dose of the osteogenesis promoter and one of foods or drinks for promoting osteogenesis of the present invention 10 mg/day or more (in terms of solid matter) of lactoperoxidase and/or a digestion product thereof. Moreover, in an osteogenesis promoter, 5 mg to 100 g/100 g (in terms of solid matter) of lactoperoxidase and/or a digestion product thereof is desirably blended, while in one of foods or drinks for promoting osteogenesis, 5 mg to 10 g/100 g (in terms of solid matter) of lactoperoxidase and/or a digestion product thereof is desirably blended.

As described above, osteogenesis can be promoted by ingesting an osteogenesis promoter of the present invention to promote osteoblast differentiation, resulting in prevention or amelioration of various bone diseases such as osteoporosis. In addition, a bone strengthening effect is also obtained. Note that lactoperoxidase is originally a milk-derived ingredient and is confirmed to have no acute toxicity to rats.

Hereinafter, the present invention will be described in more detail by way of Examples and Test Examples for illustrative purposes only, and the present invention is not limited thereto.

EXAMPLE 1

A column (diameter 5 cm×height 30 cm) filled with 400 g of a cation-exchange resin, sulfonated Chitopearl (manufactured by Fujibo Holdings, Inc.), was thoroughly washed with deionized water, and then 40 l of unsterilized skim milk (pH 6.7) was passed through the column at a flow rate of 25 ml/min. Thereafter, the column was thoroughly washed with deionized water, and elution was performed with a 0.02 M carbonate buffer (pH 7.0) containing 1.5 M sodium chloride. Then, an eluted fraction containing lactoperoxidase was adsorbed to a S-Sepharose FF column (manufactured by Amersham Biosciences), and the column was thoroughly washed with deionized water. The column was equilibrated with a 10 mM phosphate buffer (pH 7.0), and then the adsorbed fraction was eluted using a linear gradient of 0 to 1 M NaCl, followed by collection of a fraction containing lactoperoxidase. Then, the fraction was treated by gel filtration chromatography using HiLoad 16/60 Superdex 75 pg (manufactured by Amersham Biosciences), to thereby yield 11 g of lactoperoxidase. Note that the thus-obtained lactoperoxidase has a purity of 91% and can be used as an osteogenesis promoter without modification.

EXAMPLE 2

5 mg of lactoperoxidase obtained in Example 1 was suspended in 10 ml of water, and trypsin which is a protease (manufactured by Sigma) was added so as to have a final concentration of 0.01% by weight, followed by an enzyme treatment at 37° C. for 1 hour. Then, the enzyme was inactivated by a heat treatment at 90° C. for 5 minutes and then freeze-dried, to thereby yield 4.1 mg of a lactoperoxidase digestion product. Analysis of thus-obtained lactoperoxidase digestion product by a gel filtration technique revealed that the product has a molecular weight of 10,000 or less.

TEST EXAMPLE 1

The lactoperoxidase obtained in Example 1 and the lactoperoxidase digestion product obtained in Example 2 were investigated for the osteoblast differentiation promoting effect. Specifically, human-derived preosteoblast MG63 cells in DMEM medium (manufactured by Flow Laboratories) containing 10% bovine fetal serum were inoculated to a 96-well plate at a density of $2 \times 10^4$ cells/ml and were cultured in the presence of 5% $CO_2$ at 37° C. for 4 days, and the cells were provided as test culture cells. Then, the medium was exchanged for a medium containing 1% bovine fetal serum. The lactoperoxidase solution obtained in Example 1 was added to the medium so as to have final concentrations of 10 and 100 μg/ml, while the lactoperoxidase digestion product solutions obtained in Example 2 (a solution that had been subjected to a heat treatment at 90° C. for 5 minutes and a solution that had been subjected to no heat treatment) were added to the medium so as to each have a final concentration of 100 μg/ml, followed by culture at 37° C. for 5 days. The culture supernatants were collected, and type I collagen levels in the culture supernatants were measured using a Procollagen Type I C-peptide EIA Kit (Takara MK101) to investigate the osteoblast differentiation promoting activity. A solution to which no lactoperoxidase was added was used as a control. The collagen level was represented as a proportion (%) of the type I collagen measured level of each sample to the type I collagen measured level of the control. The results are shown in Table 1.

TABLE 1

|  | Final concentration | Collagen level (%) |
|---|---|---|
| Control (No addition) | — | 100 ± 6 |
| Example 1 | 10 μg/ml | 191 ± 4 |
| Example 1 | 100 μg/ml | 188 ± 6 |
| Example 2 | 100 μg/ml | 191 ± 13 |
| Example 2 (Unheated) | 100 μg/ml | 224 ± 11 |

In the groups each to which lactoperoxidase obtained in Example 1 or the lactoperoxidase digestion product obtained in Example 2 were added, the type I collagen levels were found to increase compared with that of the control (no lactoperoxidase addition) group, and therefore they were found to have the osteoblast differentiation promoting effect.

Meanwhile, it was found that the lactoperoxidase digestion product tends to produce more type I collagens and has a stronger osteoblast proliferation activity than lactoperoxidase.

TEST EXAMPLE 2

The osteogenesis promoting activity was tested in the same way as TEST EXAMPLE 1 with the lactoperoxidase obtained in EXAMPLE 1 and the milk-derived basic protein of Patent Document 5 (lactoperoxidase content: 46.5%). The result is shown in Table 2.

TABLE 2

|  | LPO I concentratiod (%) | Final concentration | Collagen Lebel (%) |
|---|---|---|---|
| Control | 0 |  | 100 ± 6 |
| Milk-derived basic protein | 46.5 | 100 μg/ml | 134 ± 1 |
| Lactoperoxidase | 91 | 100 μg/ml | 203 ± 2 |

The osteogenesis promoting activity of milk-derived basic protein comprising lactoferrin etc was lower (100 μg/ml: 134±1) than that of lactoperoxidase of one tenth concentration (10 μg/ml: 191±4) from Tables 1 and 2. The result indicates that the composition of highly-purified lactoperoxidase can be administered in much lower level compared to the composition of lactoperoxidase of low purity to obtain better results (collagen level per 1 μg/ml of lactoperoxidase is 1.34 in Patent Document 5 and 19.1 in the present invention).

The lactoperoxidase obtained in Example 1 was investigated for the bone strengthening effect by an animal experiment. For the animal experiment, 4-week-old SD female rats were used. After preliminary feeding for 1 week, the rats were subjected to a surgery to remove their ovaries and then fed with calcium deficiency feeds for 5 weeks, and the rats were provided to the animal experiment. Note that the rats that were subjected to the surgery to remove the ovaries and fed with calcium deficiency foods for 5 weeks were clearly in an osteoporotic state.

Rats in the osteoporotic state were divided into 2 groups of 6 each: a control group (group A) to which no lactoperoxidase was added and a group (group B) to which 1.0% by weight of lactoperoxidase was administered. The rats were fed for 4 months and 1 week with test feeds shown in Table 2. Note that the respective test feeds were adjusted with casein so as to have the same nitrogen content (17.06%). Meanwhile, in each test feed, 300 mg of calcium, 230 mg of phosphorous, and 50 mg of magnesium were blended per 100 g.

TEST EXAMPLE 3

TABLE 3

|  | Group A | Group B |  |
|---|---|---|---|
| Casein | 20.0 | 18.9 | (% by weight) |
| Cornstarch | 15.0 | 15.0 |  |
| Cellulose | 5.0 | 5.0 |  |
| Corn oil | 5.0 | 5.0 |  |
| Vitamin mixture | 1.0 | 1.0 |  |
| Mineral mixture | 2.65 | 2.65 |  |
| Sucrose | 51.05 | 51.15 |  |
| DL-methionine | 0.3 | 0.3 |  |
| Lactoperoxidase (Example 1) | — | 1.0 |  |

4 months and 1 week later, the both femora and tibiae of the rats of each group were removed, and the bone strengths of the femora were measured by a bone fracture properties measuring device (Rheometer Max type RX-1600, manufactured by Aitecno Inc.). The results are shown in FIG. 1. According to FIG. 1, the breaking stress of the femora of the lactoperoxidase administered group (group B: LPO) was found to be higher than that of the control group (group A: no LPO addition).

EXAMPLE 3

(Production of Osteogenesis Promoter)

93.4 g of hydrous crystalline glucose, 5 g of calcium carbonate, 1 g of sugar ester, and 0.5 g of a flavor were added to 100 mg of lactoperoxidase obtained in Example 1 and then mixed, and the mixture was formed into tablets, to thereby produce an osteogenesis promoter of the present invention.

EXAMPLE 4

(Production of Milk Beverage for Promoting Osteogenesis)

Lactoperoxidase obtained in Example 1 was added to raw milk so as to have a concentration of 1 g/l, and the mixture was homogenized at a homogenization pressure of 120 kg/cm$^2$, followed by heat sterilization at 75° C. for 15 seconds, to thereby yield a milk beverage for promoting osteogenesis of the present invention.

EXAMPLE 5

(Production of Milk Beverage for Promoting Osteogenesis)

The lactoperoxidase digestion product obtained in Example 2 was added to raw milk so as to have a concentration of 1 g/l, and the mixture was homogenized at a homogenization pressure of 120 kg/cm$^2$, followed by heat sterilization at 75° C. for 15 seconds, to thereby yield a milk beverage for promoting osteogenesis of the present invention.

EXAMPLE 6

(Production of Drink for Promoting Osteogenesis)

40 g of lactoperoxidase obtained in Example 1 was dissolved in 50 l of deionized water having a pH adjusted to 3.2 with lactic acid and then 1 kg of sugar and 10 g of a flavor were dissolved therein, followed by heat sterilization at 90° C. for 15 seconds. 50 ml of the solution was filled in each glass bottle with a cover, and the bottle was sealed, to thereby produce a drink for promoting osteogenesis of the present invention.

EXAMPLE 7

(Production of Biscuit for Promoting Osteogenesis)

Raw materials were mixed at a rate of lactoperoxidase obtained in Example 1 0.005 (% by weight), flour 50.0 (% by weight), sugar 20.0 (% by weight), salt 0.5 (% by weight), margarine 12.5 (% by weight), egg 12.1 (% by weight), water 4.1 (% by weight), sodium hydrogencarbonate 0.1 (% by weight), ammonium bicarbonate 0.2 (% by weight), and calcium carbonate 0.5 (% by weight), to make a dough. The dough was shaped and baked, to thereby produce a biscuit for promoting osteogenesis of the present invention.

EXAMPLE 8

(Production of Jelly for Promoting Osteogenesis)

Raw materials were mixed at a rate of lactoperoxidase obtained in Example 1 0.0005 (% by weight), fructose 20.0 (% by weight), granulated sugar 15.0 (% by weight), starch syrup 5.0 (% by weight), agar 1.0 (% by weight), a flavor 0.11 (% by weight), calcium 0.1 (% by weight), and water 58.79 (% by weight). Then the mixture was filled into a container, followed by heat sterilization, to thereby produce a jelly for promoting osteogenesis of the present invention.

EXAMPLE 9

(Production of Processed Cheese for Promoting Osteogenesis)

Raw materials were mixed at a rate of lactoperoxidase obtained in Example 1 0.005 (% by weight), Gouda cheese 43.0 (% by weight), Cheddar cheese 43.5 (% by weight), sodium citrate 2.0 (% by weight), milk-derived calcium 1.0 (% by weight), and water 10.5 (% by weight). The mixture was emulsified at 85° C., to thereby produce a processed cheese for promoting osteogenesis of the present invention.

EXAMPLE 10

(Production of Infant Formula for Promoting Osteogenesis)

Raw materials were mixed at a rate of lactoperoxidase obtained in Example 1 0.001 (% by weight), skim milk 75.61 (% by weight), a whey protein concentrate 2.36 (% by weight), lactose 13.86 (% by weight), a mineral mixture 0.32 (% by weight), a water-soluble vitamin mixture 0.32 (% by weight), and fats containing fat-soluble vitamins 7.53 (% by weight), to thereby yield infant formula for promoting osteogenesis of the present invention.

EXAMPLE 11

(Production of Dog Food)

Raw materials were mixed at a rate of lactoperoxidase obtained in Example 1 0.001 (% by weight), soybean cake 12.0 (% by weight), skim milk powder 14.0 (% by weight), soybean oil 4.0 (% by weight), corn oil 2.0 (% by weight), palm oil 28.0 (% by weight), corn starch 15.0 (% by weight), flour 9.0 (% by weight), bran 2.0 (% by weight), a vitamin mixture 9.0 (% by weight), a mineral mixture 2.0 (% by weight), and cellulose 3.0 (% by weight), to thereby produce a dog-breeding feed (dog food) for promoting osteogenesis of the present invention.

Industrial Applicability

An osteogenesis promoter which includes lactoperoxidase and/or a digestion product thereof as an effective component, and foods, drinks, drugs, feeds, or the like for promoting osteogenesis which contain lactoperoxidase and/or a digestion product thereof of the present invention promote osteoblast differentiation to promote an osteogenesis effect, so that they are useful for bone strengthening of a human or livestock and useful for preventing or ameliorating various bone diseases such as osteoporosis.

The invention claimed is:

1. A method of osteogenesis promotion by administering to a human by oral ingestion an effective amount of lactoperoxidase having a purity of 91%.

2. The method of osteogenesis promotion according to claim 1, wherein the lactoperoxidase having a purity of 91% is administered by oral ingestion at the effective amount of 10 mg/day or more.

3. A method of osteogenesis promotion comprising mixing an effective amount of lactoperoxidase having a purity of 91% with food, drink, drug, or feed and administering said food, drink, drug or feed mixed with the lactoperoxidase having a purity of 91% to a human or an animal.

4. The method of osteogenesis promotion according to claim 3, wherein the lactoperoxidase having a purity of 91% is administered at the amount of 10 mg/day or more.

\* \* \* \* \*